US009492085B2

(12) United States Patent
Vyssotski et al.

(10) Patent No.: US 9,492,085 B2
(45) Date of Patent: Nov. 15, 2016

(54) INTEGRATED SELF-CONTAINED RECORDER OF BIOLOGICAL DATA FOR SMALL ANIMAL RESEARCH

(76) Inventors: Alexei L. Vyssotski, Zurich (CH); Dmitri L. Vyssotski, Tarrytown, NY (US)

( * ) Notice: Subject to any disclaimer, the term of this patent is extended or adjusted under 35 U.S.C. 154(b) by 0 days.

(21) Appl. No.: 13/427,441

(22) Filed: Mar. 22, 2012

(65) Prior Publication Data

US 2012/0179386 A1   Jul. 12, 2012

Related U.S. Application Data

(62) Division of application No. 11/550,587, filed on Oct. 18, 2006, now Pat. No. 8,160,688.

(60) Provisional application No. 60/744,737, filed on Apr. 12, 2006.

(51) Int. Cl.
*A61B 5/00*   (2006.01)

(52) U.S. Cl.
CPC ...... *A61B 5/0002* (2013.01); *A61B 2560/0431* (2013.01)

(58) Field of Classification Search
CPC .... A61B 5/0002; A61B 5/0432; A61B 5/68; A01K 15/02; A01K 29/005
USPC ................................. 600/508, 509, 529, 536
See application file for complete search history.

(56) References Cited

U.S. PATENT DOCUMENTS

| | | | |
|---|---|---|---|
| 4,852,573 A | 8/1989 | Kennedy | |
| 5,191,891 A | 3/1993 | Righter | |
| 5,613,495 A | 3/1997 | Mills et al. | |
| 5,678,559 A | 10/1997 | Drakulic | |
| 6,113,539 A * | 9/2000 | Ridenour | A61B 5/0002 128/903 |
| 6,381,481 B1 | 4/2002 | Levendowski et al. | |
| 6,402,692 B1 * | 6/2002 | Morford | 600/301 |
| 6,459,936 B2 | 10/2002 | Fischell et al. | |
| 6,569,092 B1 * | 5/2003 | Guichon et al. | 600/300 |
| 6,577,893 B1 | 6/2003 | Besson et al. | |
| 6,626,676 B2 | 9/2003 | Freer | |
| 6,647,296 B2 | 11/2003 | Fischell et al. | |

(Continued)

FOREIGN PATENT DOCUMENTS

WO    WO 03/03051 A2    4/2003

OTHER PUBLICATIONS

Andrews, R.D., "Instrumentation for the remote monitoring of physiological and behavioral variables", J. Applied Physiology, 1998, pp. 1974-1981, vol. 85.

(Continued)

*Primary Examiner* — William Levicky
(74) *Attorney, Agent, or Firm* — Polsinelli PC

(57) ABSTRACT

An apparatus and method for the recording of physiological variables in small animals are described. The apparatus is an integrated self-contained recorder including a converter of biological signals into a digital form, a data storage unit, a data output for transporting the stored data from the recorder after the end of recording session, a power source and an electrical connector arranged for connection of the recorder with at least one sensor of biological signal and mechanical fixation of the recorder at the head of an animal. The recorder may contain a sensor, which receives signals from an external source for synchronization of the stored data with external equipment or observed/registered animal behavior.

30 Claims, 16 Drawing Sheets

(56) References Cited

U.S. PATENT DOCUMENTS

| | | | |
|---|---|---|---|
| 6,654,633 B2 | 11/2003 | Stengel et al. | |
| 7,551,952 B2 | 6/2009 | Gevins et al. | |
| 7,673,587 B2 | 3/2010 | Davies | |
| 2001/0050062 A1* | 12/2001 | Isley | A01K 29/005 119/712 |
| 2002/0188216 A1 | 12/2002 | Kayyali et al. | |
| 2003/0024482 A1* | 2/2003 | Gondhalekar | A01K 1/031 119/417 |
| 2003/0088161 A1* | 5/2003 | Stengel | A61B 5/002 600/301 |
| 2003/0171685 A1 | 9/2003 | Lesser et al. | |
| 2004/0133118 A1 | 7/2004 | Llinas | |
| 2004/0210156 A1 | 10/2004 | Hogan | |
| 2004/0215286 A1* | 10/2004 | Stypulkowski | A61N 1/37211 607/48 |
| 2005/0027207 A1 | 2/2005 | Westbrook et al. | |
| 2005/0085872 A1 | 4/2005 | Yanagihara et al. | |
| 2005/0124848 A1 | 6/2005 | Holzner | |
| 2005/0131288 A1 | 6/2005 | Turner et al. | |
| 2005/0165323 A1 | 7/2005 | Montgomery et al. | |
| 2005/0197590 A1 | 9/2005 | Osorio et al. | |
| 2005/0284413 A1 | 12/2005 | Boesch et al. | |
| 2006/0000420 A1 | 1/2006 | Davies | |
| 2006/0079773 A1 | 4/2006 | Mourad et al. | |
| 2006/0100530 A1 | 5/2006 | Kliot et al. | |
| 2006/0122529 A1 | 6/2006 | Tsau | |
| 2006/0173259 A1 | 8/2006 | Flaherty et al. | |
| 2006/0195042 A1 | 8/2006 | Flaherty | |
| 2007/0048707 A1 | 3/2007 | Caamano et al. | |
| 2007/0106170 A1 | 5/2007 | Dunseath et al. | |
| 2007/0191727 A1 | 8/2007 | Fadem | |
| 2007/0255176 A1* | 11/2007 | Rondoni | A61B 5/202 600/573 |
| 2008/0082019 A1 | 4/2008 | Ludving et al. | |
| 2008/0114263 A1 | 5/2008 | Topp et al. | |
| 2008/0300510 A1 | 12/2008 | Schwyn et al. | |
| 2008/0306397 A1 | 12/2008 | Bonmassar et al. | |
| 2008/0319282 A1 | 12/2008 | Tran | |

OTHER PUBLICATIONS

Mavoori, J., et al., "An autonomous implantable computer for neutral recording and stimulation in unrestrained primates", J. Neurosci. Methods, 2005, pp. 71-77, vol. 148, No. 1.

Vyssotski, A.L., et al., "Minature Neurologgers for Flying Pigeons: Multichannel EEG and Action and Field Potentials in Combination With GPS Recording", J. Neurophysiol., 2005, pp. 1263-1273, vol. 95.

Office Action for U.S. Appl. No. 11/550,587 dated Feb. 26, 2009 (36 pages).

Office Action for U.S. Appl. No. 11/550,587 dated Oct. 29, 2009 (14 pages).

Office Action for U.S. Appl. No. 11/550,587 dated Apr. 8, 2010 (11 pages).

Office Action for U.S. Appl. No. 11/550,587 dated Oct. 25, 2010 (15 pages).

Song W., et al., A Wireless Miniature Device for Neural Stimulating and Recording in Small Animals, ICNC 2006, Part II, LNCS 4222, pp. 884-893, 2007 (10 pages).

* cited by examiner

FIG. 3(A)
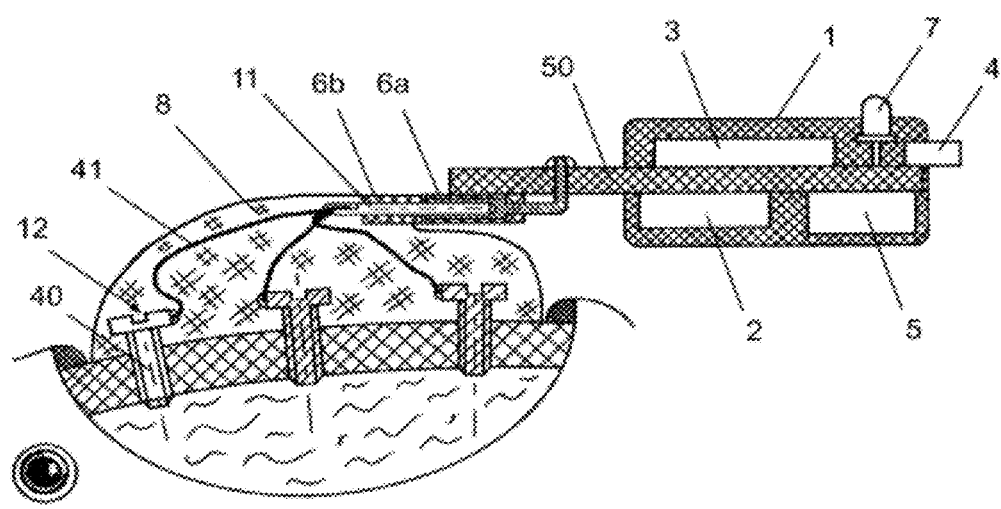
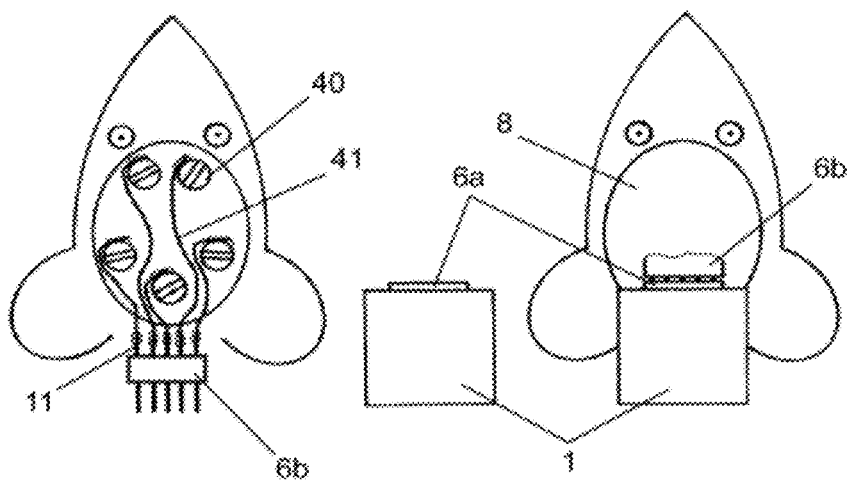
FIG. 3(B)   FIG. 3(C)

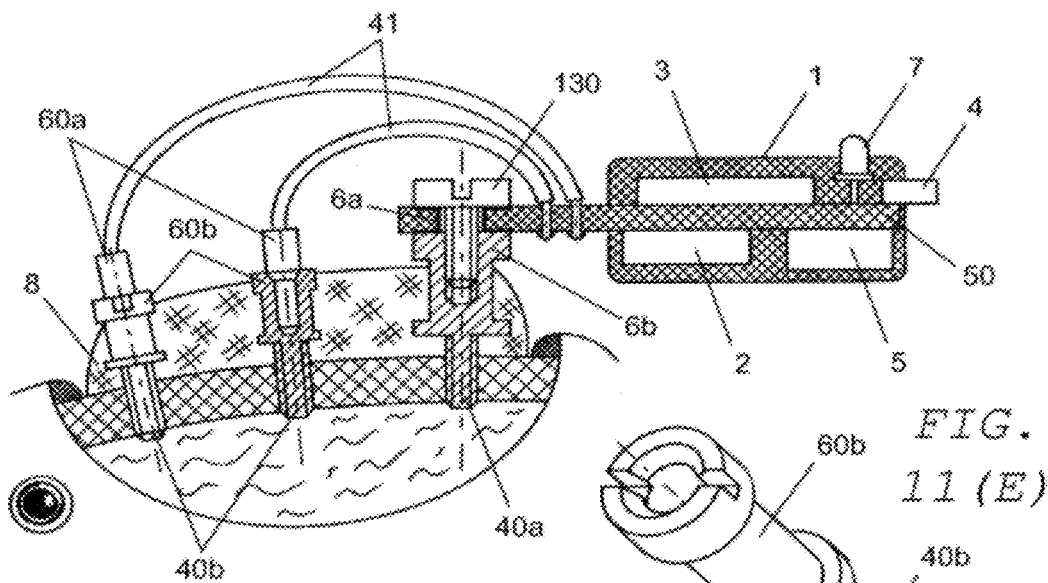
FIG. 11(A)
FIG. 11(E)
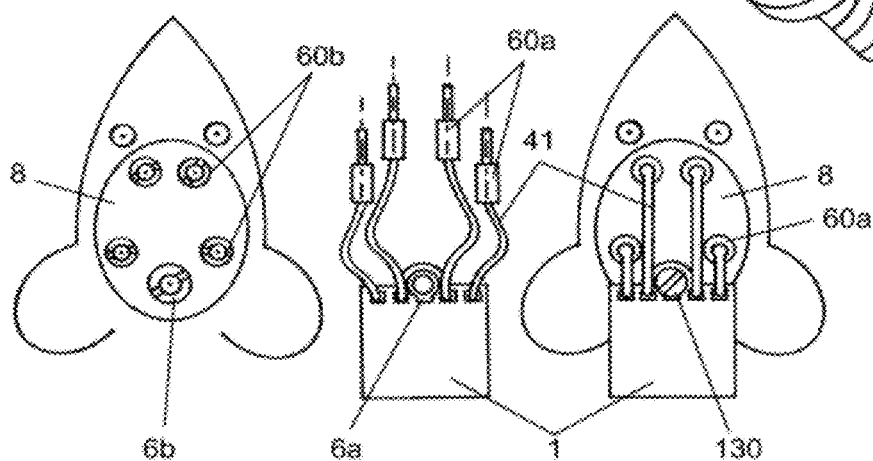
FIG. 11(B)   FIG. 11(C)   FIG. 11(D)

INTEGRATED SELF-CONTAINED RECORDER OF BIOLOGICAL DATA FOR SMALL ANIMAL RESEARCH

CROSS REFERENCE TO RELATED APPLICATION

This application is a divisional patent application of U.S. patent application Ser. No. 11/550,587 filed Oct. 18, 2006 which claims priority to U.S. Provisional Patent Application No. 60/744,737 filed Apr. 12, 2006.

FIELD OF THE INVENTION

The present invention relates to autonomous self-contained systems for the recording of biological data of small animals for research purposes.

BACKGROUND OF THE INVENTION

A large number of scientific investigations are now performed on small animals, such as rats and mice. Typical topics of the research are pre-clinical testing of pharmacological substances and the investigation of molecular cascades in the living organisms by the fabrication of genetically modified animals (that have an altered expression of the molecules of interest).

Currently, more and more researchers use mice in the laboratories. There are several reasons for this. The first reason is purely economical: mice-keeping is much cheaper than keeping rats, cats, pigs, or primates. The second reason has a scientific background: the production of genetically modified mice is faster and cheaper than rats or other larger animals. Mice have short generation times, and tools exist for research purposes for mice. The exploitation of mice in such types of research has become a standard de facto.

Researchers are usually interested in the influence of a particular pharmacological agent or a genetic modification on the living organism. The primary indicators of such influence are changes in behavior. These changes are evidence of a biological activity of the substance in question or of the importance of a gene whose expression has been modified. Thus, behavioral testing of animals is an essential part of modern biological research.

Let us suppose that the behavior of a treated group of animals is changed. What can it tell us about the action of pharmacological substance? If a molecular cascade in which the investigated substance is involved is known, one often can derive a conclusion. However, in many cases there are only suggestions about the role of the new substance. In such cases, additional investigation is required. The next step in research is the detection of alterations in the organism. The study can be started practically at any level (biochemical, morphological, anatomical, physiological), but a particular choice is usually driven by a working hypothesis and technical capabilities.

The next logical step after a purely behavioral approach is a registration of alterations in physiological parameters of behaving animals. This step was often omitted in small animals because of technical limitations. Biological sensors and recording means were just too big to be attached and carried by small animals.

Animal behavior is controlled by the brain. The brain is a main target for many pharmacological substances. Because of this, it currently attracts more attention by researchers than any other organ. At present, the recording of electrical brain activity in mice, such as brain waves (electroencephalogram), neuronal action and field potentials, is conducted exclusively by means of wires attached to the head transmitting signals to stationary equipment. Such an arrangement is disturbing for the animals. It is also difficult to conduct such experiment during a prolonged period of time, as there is a risk that a connecting cable will be destroyed by the rodent. Such a cable also prevents the conducting of behavior-physiological experiments in some environments, for instance, in some mazes and big arenas.

Known radio telemetric systems eliminate cabling, but they need significant amount of energy for transmission of electrophysiological data, or require a receiving antenna of an unpractical size and geometry. The requirement of significant amount of energy limits the duration of an experiment and the relatively large size of the antenna prevents conducting of the experiment in certain environments. A typical Bluetooth short-range (10 m) radio transmitter consumes around 60 mA at its standard transmission rate of 721 kbps. A specially engineered biological transmitter can consume less power than a Bluetooth transmitter, but still requires substantial power, especially at high data transmission rates. The problem of high power consumption of radio transmitters has been partially solved by Yanagihara et al. (U.S. Pat. Pub. 2005/0085872 A1, April 2005). These authors suggest accumulating information temporarily in the transmitting device in local data storage, and then sending the stored data in a packet, while switching on the transmitter only during packet sending. This allows the researcher to exploit the transmitter in its optimal mode, i.e., to fully fill its bandwidth with the data. However, a higher transmission rate requires more power. Thus, this solution does not fully solve the problem of high power consumption of radio telemetry devices and techniques.

Another obstacle in using telemetric devices in such small animals as mice is the size of the transmitting module. The modules have become much smaller in the last several years. However, they are still too big to be carried at the head of a mouse, especially when considering that an additional signal-conditioning circuitry and a power source are needed. For instance, one of the smallest Bluetooth transmitters has dimensions 11.8×17.6×1.9 mm, including antenna (Mitsumi, WML-09). An example of transmitter attachment to the head of a rat is presented in the U.S. Pat. No. 4,852,573 (Kennedy, August 1989). Alternative methods of device attachment, such as attaching the device to the animal body or implanting it inside the animal, have severe disadvantages. Attaching a backpack disturbs the animal. Wires that go from the back pack to the head are in an extremely weak place and need protection. They can be damaged very quickly by the animal. Implantation of the device together with the wires under the skin or into the abdominal cavity (Bornhoft et al., WO 03/030581 A2, April 2003) is painful for the animal. This process generally requires at least five days of anesthetic treatment after such operation.

An additional disadvantage of telemetry is the interference of signals from several subjects in an experimental room. This is required, for instance, in sleep research. Signals from different devices attached to the several subjects should be transmitted in different frequency bands or should somehow be temporarily multiplexed. In a digital wireless network, one has to pay attention to not exceed the bandwidth of a receiver. This significantly increases the complexity of the entire experimental setup.

An alternative method is a data logging—when recorded variables are stored locally in the device and are downloaded at the end of a recording session by means of a standard wired interface. This method has become feasible due to profound progress in microelectronics during the last several years. Data logging has been implemented for patient monitoring in hospitals (Drakulic, U.S. Pat. No. 5,678,559, October 1997; Turner et al., U.S. Pat. Pub 2005/0131288 A1, June 2005) and also in animal research (Andrews, R. D., "Instrumentation for the remote monitoring of physiological and behavioral variables", J. Appl. Physiol. 1998 November; 85(5):1974-81; Mavoori, J., et al., "An autonomous implantable computer for neural recording and stimulation in unrestrained primates", J. Neurosci. Methods. 2005 October 15; 148(1):71-7; Vyssotski, A. L., et al., "Miniature neurologgers for flying pigeons: multichannel EEG and action and field potentials in combination with GPS recording", J. Neurophysiol. 2006 February; 95(2):1263-73) (the Vyssotski article is hereby incorporated by reference in its entirety).

There are two main advantages of data logging in comparison with radio telemetry: low power consumption (even at high data rates) and very small size of the data storage. A typical commercially available 1.8V NAND Flash memory, which can be used in a transportable animal data logger, consumes 2 mA at a storing data rate of 60 kilobytes per second. Such dataflow is typically produced by four electrodes recording neuronal activity at a smallest allowed acquisition setup data rate of 10 ksps and 12-bit ADC resolution. Such current consumption is only 1/30 of the current consumption of a Bluetooth transmitter and, and at the same time, such data flow would practically completely occupy the Bluetooth's bandwidth. Thus, with the same battery, a data logger would run 30 times longer than a radio transmitter. A typical NAND Flash 256 MB memory chip in a FBGA cage has size of only 9.5×12.0×1.2 mm. The volume occupied by the memory module is almost 3 times smaller than a volume occupied by the smallest Bluetooth radio transmitter. The 256 MB of memory is enough to store 4 EEG channels during 5 days (100 samples per second/channel) or 4 channels of neuronal activity (neuronal spikes) during 1 h 10 min (10 kilo samples per second/channel). The duration of neuronal activity registration is enough for most short-term behavioral tests. Five days of non-stop EEG record can be useful in sleep research and also in monitoring disease development, for instance, under pharmacological treatment, and to test the efficacy of a pharmacological agent. If one needs a more prolonged registration period, the device can be exchanged with another one within several seconds. It does not significantly affect the continuity of the record.

In spite of very attractive features of data logging, it also suffers from a set of minor disadvantages. In spite of the extremely small size of the device, a mouse head is so small that the data logging device needs a special way of attachment to the head.

Another disadvantage is the absence of a synchronizing link between the data logging device and external devices. In many cases a researcher needs to know not only the state of the animal, but also the external conditions under which animal was in this state. If the animal receives some stimulation or demonstrates some behavior, one should precisely know which time points of the stored record in the data logging device corresponds to stimulus application times or behavioral episodes. Synchronization of the start of the recording with an external clock is not always sufficient, especially if some rapid neuronal responses are to be investigated. Mavoori et al. (2005) supplemented a data logger with an IR-link for this purpose. In his setup IR pulses were sent to the external equipment when neuronal spikes were detected. They were stored together with other behavioral information in an ordinary computer. The first disadvantage of such approach is its redundancy: some amount of data occurred was stored two times—in the logger and in the external device. The logger stores more data than it transmits via IR-link: the spike form occurred stored only in the logger. Such distributed accumulation of the experimental data increases the complexity of the subsequent analysis. The second disadvantage is that a wireless IR communication requires a direct line of sight between receiver and transmitter. This requirement is very difficult to fulfill with a free-moving animal. Thus, such type of communication is unreliable. The third disadvantage of this solution is that an IR transmitter also suffers from high power consumption as a radio transmitter, even if it transmits in short "bursts". Peak current of a typical low-power IR transmitter is equal to 60 mA. As such, we conclude that such type of synchronizing communication cannot be used in a small mouse-fit data logger. A power-saving and economical way of synchronizing of the data logger with external events is an aspect of the current invention.

SUMMARY OF THE INVENTION

A first embodiment of the present invention includes an integrated self-contained recorder of biological data for a small animal, comprising: a converter for conversion of at least one biological signal to digital data, a data storage unit for storing the digital data, a data output capable of transporting the stored digital data from the recorder after the recording session, a power source, a head connector that attaches to a head of a small animal, the head connector comprising at least one sensor of a biological signal from the small animal, and an electrical connector for connecting the recorder with the head connector. The electrical connector provides for mechanical fixation between the head connector and the recorder. In other embodiments, the data output may be exchanged with a removable data storage unit, such as a memory card.

A second embodiment of the present invention includes an integrated self-contained recorder of biological data comprising: a converter for conversion of at least one biological signal to digital data, a sensor capable of receiving a signal from an external source for synchronization of the digital data with an external event, a data storage unit for storing the digital data and information received from the external event, a data output capable of transporting the stored digital data from the recorder after the recording session, and a power source.

The present invention overcomes two significant problems in applying data logging technology to small animals. The first problem is caused by the strict spatial limitations of the subject animal's head, i.e., the animal's head is so small that there is practically no space for mechanical attachment of the body of the data logger. The problem is solved by using an electrical connector for mechanical fixation of the recorder to the head. The head connector is affixed or attached to the animal's head. The head connector contains the sensor for detecting the biological signal. The recorder is mechanically affixed to the head connector via the electrical connector. After the data storage unit is full, the recorder may be removed from the small animal by detaching the electrical connector from the head connector. If desired, the removed recorder may be quickly replaced with another recorder.

The second problem is caused by limited size and capacity of the power source of the ultra-miniature data logger and necessity of synchronization of the recorded data with external events. Limited capacity of the power source practically excludes any possibility of telemetric transmission of information from the device outside, because known transmitters (infrared-based or radio-based) have high power consumption. The solution is to transmit synchronizing information from the external equipment and store it in the logger together with physiological data. Power limitations do not exist for the transmitter connected to external stationary equipment as the transmitter may receive power directly from an alternating current source such as a wall outlet or other storage source of power. Importantly, a receiver (IR or radio) consumes much less power than a corresponding transmitter. For instance, an infrared receiver can consume only 0.1 mA whereas the power consumption of an IR transmitter is 60 mA. Thus, such receiver can be easily implemented in a miniature logger with a limited battery capacity.

BRIEF DESCRIPTION OF THE DRAWINGS

FIGS. 3(a)-3(c) depict the integrated self-contained recorder attached to the head of a mouse.

FIGS. 11(a)-11(e) show an alternative attachment of the recorder by means of one centrally positioned screw providing an electrical connectivity with one sensor of biologic signal.

DETAILED DESCRIPTION OF THE INVENTION

Reference will now be made in detail to the preferred embodiments of the present invention, examples of which are illustrated in the accompanying drawings.

Figure 1:
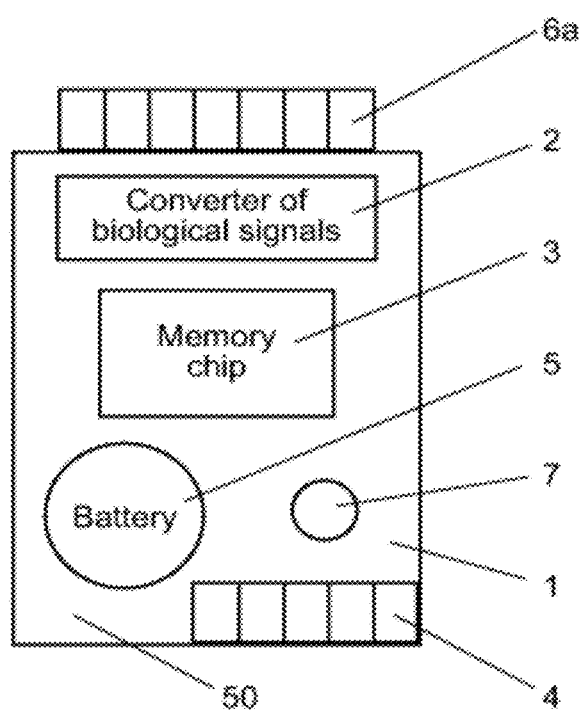
FIG. 1 is a configuration view showing an integrated self-contained recorder of biological data for small animal research according to one embodiment of the invention.
Figure 2:
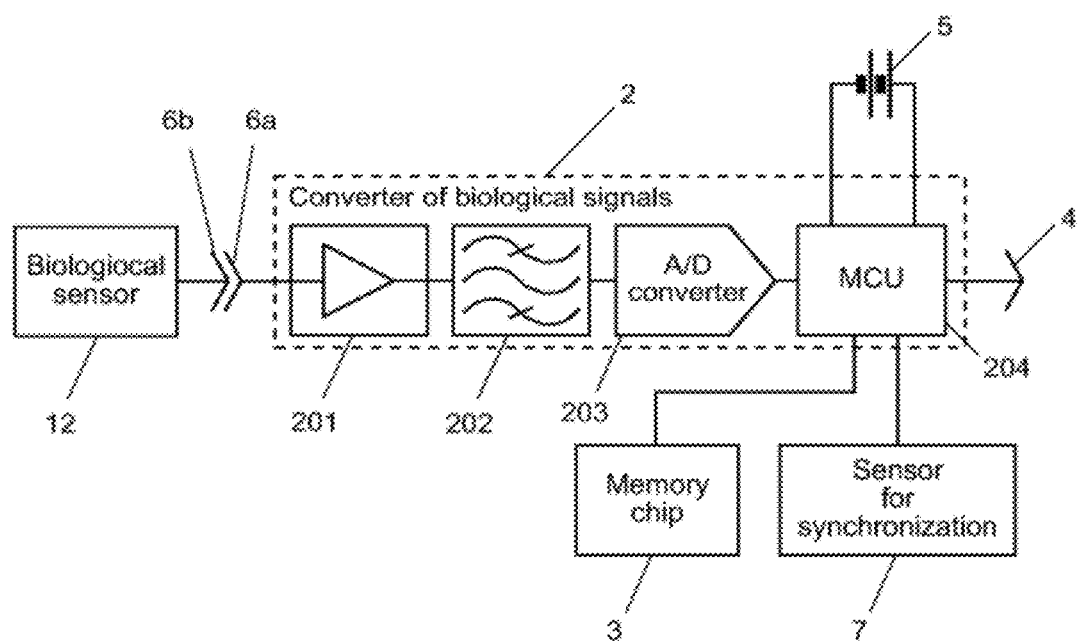
FIG. 2 is a schematic block diagram of an inside structure of the integrated self-contained recorder.

With reference to FIGS. 1-3, an integrated self-contained recorder 1 of biological data for small animals research of the present invention is shown. The recorder 1 includes a converter 2 for converting at least one biological signal to digital data, a data storage module 3 for storing the digital data, a data output 4 capable of transporting the stored digital data from the recorder 1 after a recording session, a power source 5, an electrical connector 6a for connection of the recorder 1 with a head connector 6b, at least one sensor of biological signal 12, and a sensor 7 capable of receiving a signal from an external source for synchronization of the digital data with an external event.

The electrical connector 6a connects the recorder 1 to the head connector 6b, which includes the biological sensor 12. The head connector 6b is affixed to the head of the animal and places the biological sensor 12 in contact with the head of the animal. The electrical connector 6a has a complementary structure to receive and to connect to the head connector 6b for the transfer of biological signals from the biological sensor 12 to the converter 2. The converter 2 receives signals of physiological parameters from the biological sensor 12 attached to the animal's head through electrical connector 6a and the head connector 6b. The main usage of the device 1 is the monitoring of electrical brain activity. Thus, the above-mentioned sensors 12 are usually electrodes for brain activity registration.

Figure 4:
FIG. 4 is a photograph of an attachment of the integrated self-contained recorder at the head of the mouse, frontal view.
Figure 5:
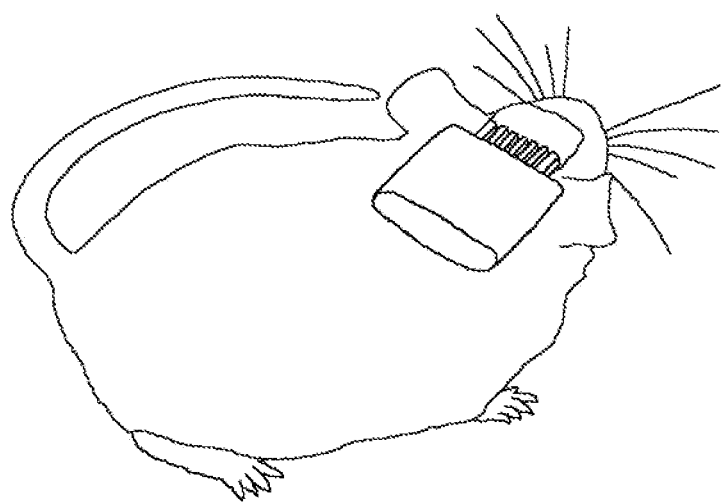
FIG. 5 is a photograph of an attachment of the integrated self-contained recorder at the head of the mouse, rear view.
Figure 6:
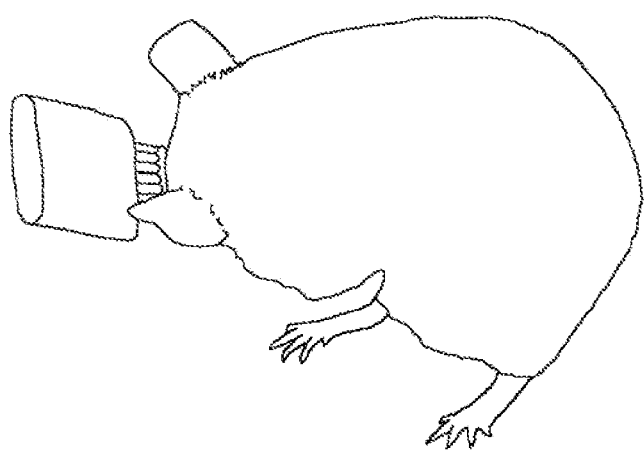
FIG. 6 is a photograph of an attachment of the integrated self-contained recorder at the head of the mouse, rear view during grooming behavior.
Figure 7:
FIG. 7 is a photograph of an attachment of the recorder at the head of a pigeon.

The second important function of the electrical connector 6a and the head connector 6b is the mechanical fixation of the device 1 to the animal's head, as shown in FIGS. 2-5. The head connector 6b is fixed to the animal's skull with a hardened adhesive 8 (as depicted in FIGS. 6-7), such as dental cement. Dental acrylic cement is also typically used for fixation of the electrodes (epidural, intracranial) to the animal's head.

With reference to FIG. 2, the converter 2 of biological signals contains analog conditioning circuitry for amplification 201 and band-pass filtering of electrical signals 202, an analog-digital converter (ADC) 203, and a microcontroller 204 programmed to receive data from the ADC and store the data in a non-volatile memory module, namely the data storing module 3. The data storage module 3 may be a nonvolatile integrated circuit memory chip. Alternatively, the microcontroller may contain a built in ADC.

The data storing module 3 may be a NAND flash memory chip or a removable memory card, for example Secure Digital (SD) or Multimedia (MMC) card. A removable card may be used for transporting stored data to a standard computer for analysis at the end of an experiment. If a fixed (soldered) memory chip is used, a data output connector 4 should be used for data downloading under control of the microcontroller of the recorder. For this purpose the built in microcontroller may be linked with an external standard computer by a serial link. This link can be an asynchronous UART-based (Universal Asynchronous Receiver Transmitter) or synchronous SPI-based (Serial Peripheral Interface). An external standard computer should have an appropriate interface adapter, or converter to convert serial interface to more common USB bus. An alternative solution is an implementation of a microcontroller with already built in USB interface. If a removable memory card is used, the data output connector 4 will include a slot to receive the memory card and electrically connect it to the microcontroller.

The power source 5 may be a coin cell battery, usually non-rechargeable, a lithium polymeric rechargeable battery, a thin film battery, a capacitor, or other electrical storage devices suitable for the present invention. The main advantage of non-rechargeable batteries is their small weight. Usually, non-rechargeable batteries are two times lighter than rechargeable batteries of equal capacity and voltage. However, appropriate means for fixation and replacement of these batteries should be implemented. Rechargeable batteries may be built in to device and easily encapsulated together with the other electronics in a waterproof container or compound. This is very important advantage in some situations.

The sensor 7 may be a microcontroller-polled sensor for synchronization with external stationary scientific equipment 35. The sensor 7 may be an acoustic sensor, e.g., a microphone. The sensor 7 is built into the recorder 1. Preferred embodiments of the sensor 7 include an optical sensor, for example, an infrared phototransistor, and a miniature radio antenna with an appropriate supplementary circuitry receiving radio waves.

The sensor 7 receives a synchronizing signal that may be sent from a variety of sources, such as the stationary scientific equipment 35, or be initiated by various events. The synchronizing signal may contain information. For example, the synchronizing signal may contain information about the animal's location or the spatial coordinates of the animal. The synchronizing signal may also contain a time record. The synchronizing signal may be set manually by an operator, by a computer, or by an animal action, such as the animal changing location, pressing on a lever or crossing an infrared beam. The synchronizing signal may be provided by a computer, wherein the computer receives information about animal location via video camera or the computer receives information about animal location via an intersection of infrared beams by the animal's body. In certain embodiments, the computer analyses animal behavior, splits it in into behavioral episodes, classifies behavioral episodes and sends labels of these episodes to the recorder.

The sensor 7 periodically, and when status of the sensor 7 changes, stores a label of this event in the digital data record. Such labels can be detected in the record during its analysis. This allows the researcher to align the recorded brain activity with the stimulation of the animal during an experiment. The stimulation may be from a light signal, a sound signal, or an electric signal. This solution increases the field of applicability of the described recorders, as such synchronization is highly desirable in experiments with quick response investigation, or when precise timing of stimuli is difficult to realize in the external equipment.

The converter 2, the data storage 3, the data output 4, the power source 5 and the sensor 7 are connected to a board 50. The board 50 may form a non-flexible combination of its elements. The electrical connector 6a may rigidly attach to the board 50. Other electrical components may be added to the board 50.

With reference to FIG. 3, the head connector 6b includes the biologic sensor 12. The biologic sensor 12 includes electrodes 40 which are fixed to the animal's skull with dental cement. The biological sensor 12 may include one or more electrodes 40. Suitable electrodes 40 include gold-plated epidural screw electrodes or 150 micrometer, varnish covered nichrome electrodes. Other electrically conductive materials may be used for the electrodes 40. Conductive wires 41, soldered from one side to the electrodes 40 and soldered from another side to contacts 11 of the connector 6b, provide electrical connection between the electrodes 40 and the head connector 6b. The head connector 6b provides electrical communication for the biologic signal from the electrodes 40 to the electrical connector 6a. The head connector 6b is mounted on the adhesive 8 made from a material that is adhesive to the skull of a mouse, such as acrylic cement. The electrodes 40 extend from the adhesive 8. The adhesive 8 forms a bottom surface to conform to the skull of the mouse.

FIGS. 4-7 depict fixation of the recorder 1 at the animal head by means of the electric connector 6a and the head connector 6b. As one can see, the present invention overcomes the spatial limitations of fixing a neurologging device to a small animal.

The illustrated embodiment of the device 1 has four channels for electroencephalogram (EEG) or action/field potential neuronal recording. The device 1, while weighing only two grams, includes all necessary filters, amplifiers, the microcontroller with ADC, 2×80 mAh Renata ZA10 batteries, the 256 MB memory chip, the protective cover and the electrical connector 6a. This combination allows the device 1 to record 4 channels of EEG (400 sps) during 30 hours or 4 channels of neuronal activity (10 ksps) during 1 hour 10 minutes from a mouse. The data recording board itself is extremely light: with a 256 MB memory chip it weighs 0.945 g, with a 128 MB memory—0.890 g only. Thus, the minimal possible weight of the recording combination (128 MB memory and two Renata ZA5 35 mAh batteries) may be as low as 1.285 g. Adding bigger batteries, a protecting cover and the head connector 6b for the fixation of the device 1 at the head increases weight of the construction up to two grams. However, even this weight is not a problem for a laboratory mouse weighing usually about 30 grams, as it is seen in FIGS. 4-6.

This invention opens a lot of opportunities for field researchers, interested in the investigation of brain activity in freely moving animals, for instance, in homing pigeons (FIG. 7).

FIGS. 8-12 represent alternative variants of fixation of the device 1 at the animal head. A device attached by means of a simple shift-in connector is not fixed in a reliable manner. Attempting to secure the device with an adhesive tape may help temporarily, but adhesive tape is not suitable for experiments requiring long-lasting recording.

Figure 8:
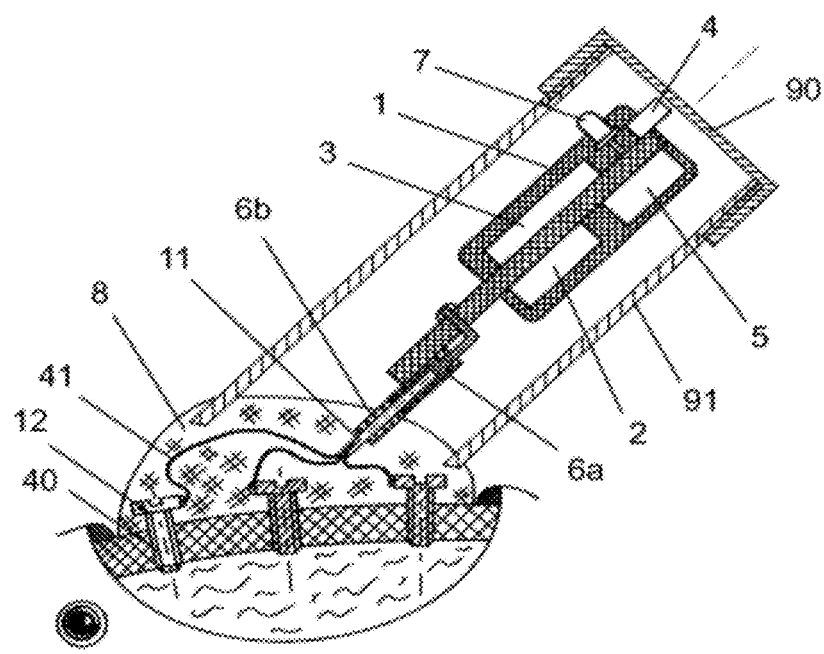
FIG. 8 shows an integrated self-contained recorder attached to the mouse head and covered by a protective tube and cup.

In order to reduce the likelihood of the head connector 6b inadvertently disconnecting from the electrical connector 6a, a screw joint may be utilized to assist in securing the electrical connector 6a to the head connector 6b. FIG. 8 shows an embodiment to reduce the likelihood of inadvertent disconnection by using a protective cup 90 with a screw joint tightened over a protective tube 91. The protective tube 91 generally surrounds the board 50. The protective tube 91 receives the protective cup 90 in a threaded engagement. When the protective cup 90 is tightened to the protective tube 91, the protective cup 90 pushes the recorder 1 with the electrical connector 6a towards the head connector 6b to assist in securing these complementary components. The protective tube 91 is fixed by dental acrylic to the head of the animal. Additionally, the cup 90 with the tube 91 protects the recorder 1 against mechanical damage and the penetration of liquids to the electrical circuits of the recorder 1 and to the electrical connector 6a and the head connector 6b. The cup 90 and the tube 91 may be made from a lightweight, durable plastic material.

Figures 9A, 9B:
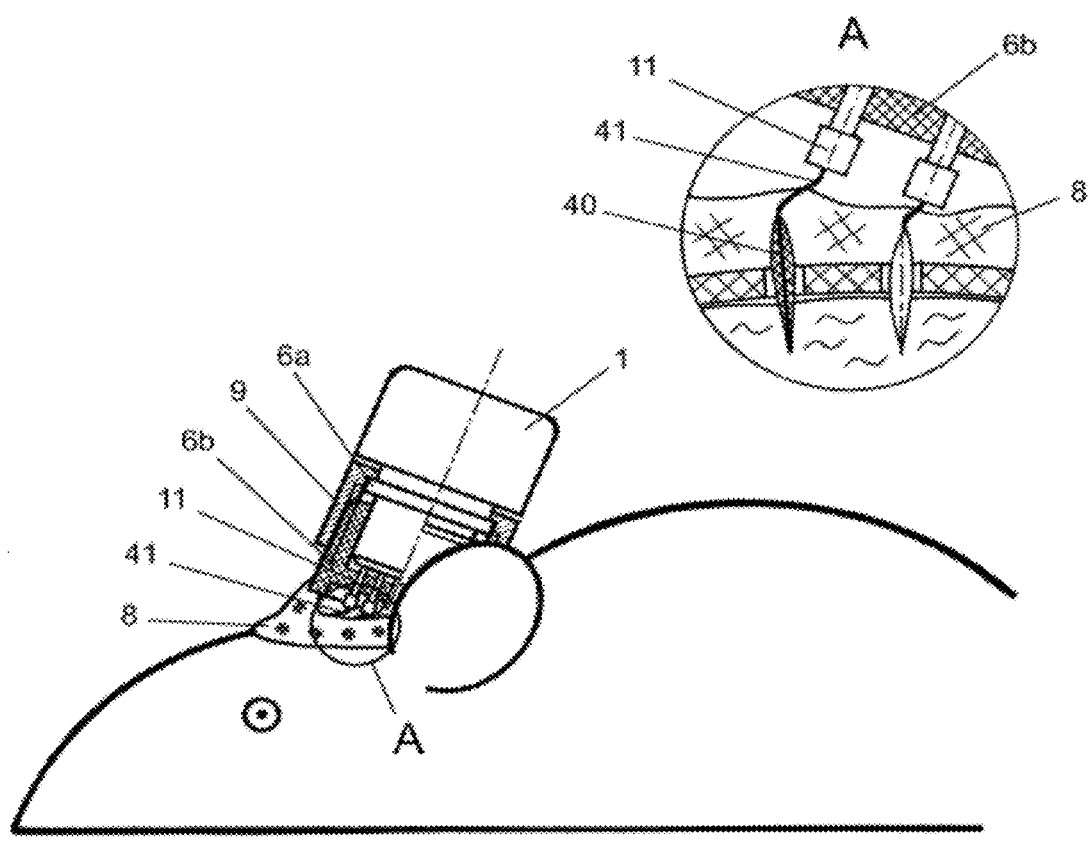
FIGS. 9(a)-9(b) depict an alternative attachment of the recorder at the head by means of a cylindrical connector with a screw joint.

FIG. 9 shows another embodiment of attachment by using a cylindrical electrical connector 6a with a screw joint for fixation of the recorder 1 at the head of an animal. Fixation is achieved by a screw ring 9 attached to the recorder 1 that provides a locking rotation. The head connector 6b is fixed to the skull by the adhesive 8. As the screw ring 9 is tightened, it forcibly holds the electrical connector 6a to the head connector 6b. Contacts 11 of the head connector 6b are connected with the electrodes 40 by conductors 41. In this illustration, intracranial electrodes 40 penetrate inside the brain to record neuronal activity.

Figure 10:
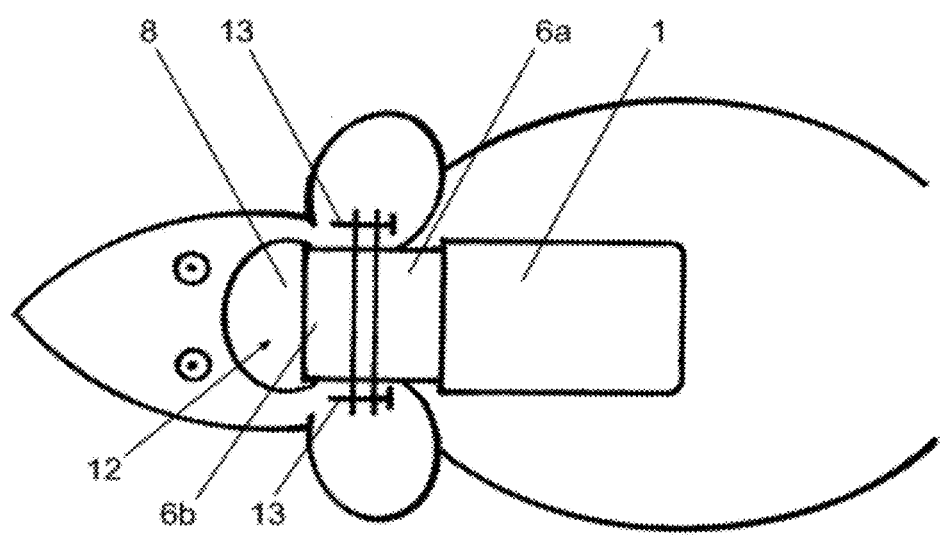
FIG. 10 depicts another alternative attachment of the recorder at the head by means of two side screws.
Figure 12:
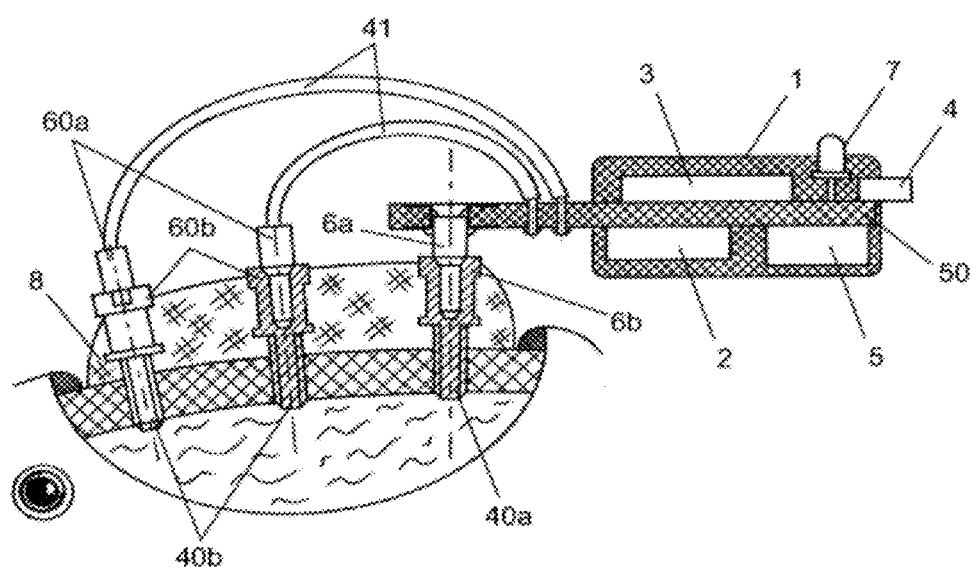
FIG. 12 shows an alternative attachment of the recorder by means of one centrally positioned single-lead shift-in connector, providing an electrical connectivity with one sensor of biological signal.

FIG. 10 shows another embodiment of a screw joint fixation of the recorder 1 at the animal head by using two side screws 13. Again, the head connector 6b is fixed at the skull by the adhesive 8. The two side screws 13 connecting the electrical connector 6a and the head connector 6b physically maintain the connection between the electrical connector 6a and the head connector 6b.

FIG. 11 shows another embodiment of a screw joint fixation of the recorder 1 at the animal head by using a centrally positioned screw 130 that mechanically tightens the electrical connector 6a with the head connector 6b. The screw 130 also provides electrical conductivity between a screw electrode 40a and the recorder 1. The screw electrode 40a is preferably a ground electrode. Again, the head connector 6b is fixed at the skull by adhesive 8. The head connector 6b also receives additional fixation by the screw electrode 40a. As shown in FIG. 11, the head connector 6b receives the screw 130. The head connector 6b transitions into screw electrode 40a. As such, the screw electrode 40a assists in joining the electrical connector 6a and the head connector 6b. Namely, the screw 130 passes through an opening of the electrical connector 6a and then threads into the head connector 6b. The tightening of the screw 130 secures the electrical connector 6a to the head connector 6b.

Other electrodes 40b are connected electrically with the recorder 1 by means of shift-in connectors 60b, leads 60a, and flexible wires 41. The shift-in connectors 60b receive the leads 60a in a frictional engagement, namely, the leads 60a are pushed into the shift-in connectors 60b. The electrodes 40b are integral with the shift-in connector 60b. This embodiment is depicted in FIGS. 11(*a*)-(*e*). As also shown, the head connector 6b and the screw electrode 40a may likewise be fabricated as one mechanical element. The benefit of such an embodiment is the simplicity of implantation of electrodes 40a, 40b with appropriate connecting parts 6b, 60b. This embodiment allows the user to avoid soldering of the wires during implantation procedure.

For short-term recording sessions (1-3 hrs), the following modification of the above-mentioned embodiment may be used. In this modification, the screw joint with the screw 130 is substituted for a shift-in connector 6a/6b with one lead (see FIG. 12). The one lead is rigidly attached (e.g., soldered) to the board 50 for fixation of the recorder 1 at the head of the animal. The above-mentioned single-lead, shift-in connector and the one lead itself can be similar to the other shift-in connectors 60b and leads 60a, depicted in FIGS. 11(*a*)-(*e*). The described modification facilitates the procedures of recorder connection and disconnection, whereas the reliability of shift-in connector is acceptable for short-term records.

Figure 13:
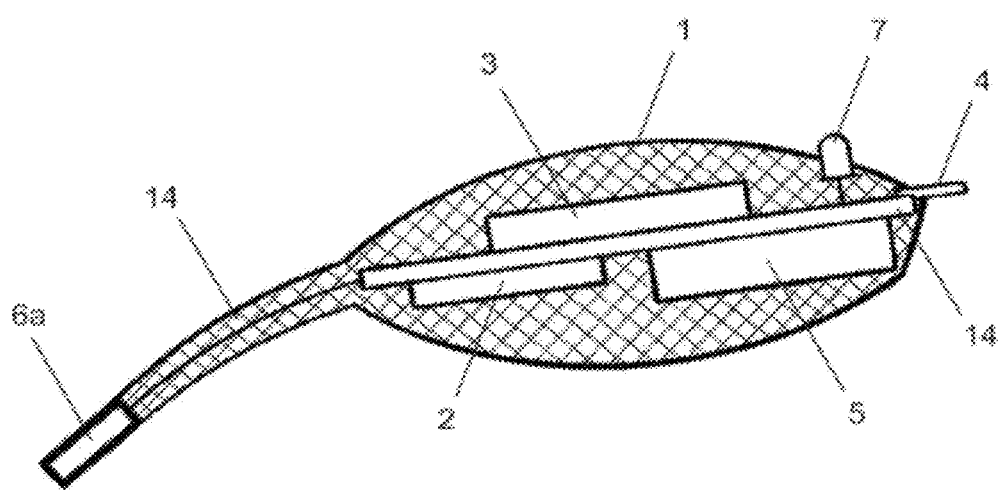
FIG. 13 is a schematic representation of an embodiment with the electrical connector attached to the recorder by means of a flexible substrate.

A solid fixation of the recorder at the animal head may restrict animal mobility in certain environments, for instance, in mazes with small connecting openings. To overcome this problem (see FIG. 13), it is proposed to connect the main part of the recorder 1 (including the converter 2, the data storage 3, the data output 4, the power source 5 and the sensor 7 for synchronization of the recorder 1 with external equipment all connected to the board 50) with the electrical connector 6a by means of a flexible substrate 14. A flexible substrate 14 will allow limited movements of the recorder 1 relatively to the animal head mainly in the up-down direction. This will decrease disturbances of an experimental animal associated with carrying of such equipment. The flexible substrate comprises polyimide or polyester material that wraps or covers the electrical wiring between the electrical connector 6a and the main part of the recorder 1.

Figure 14:
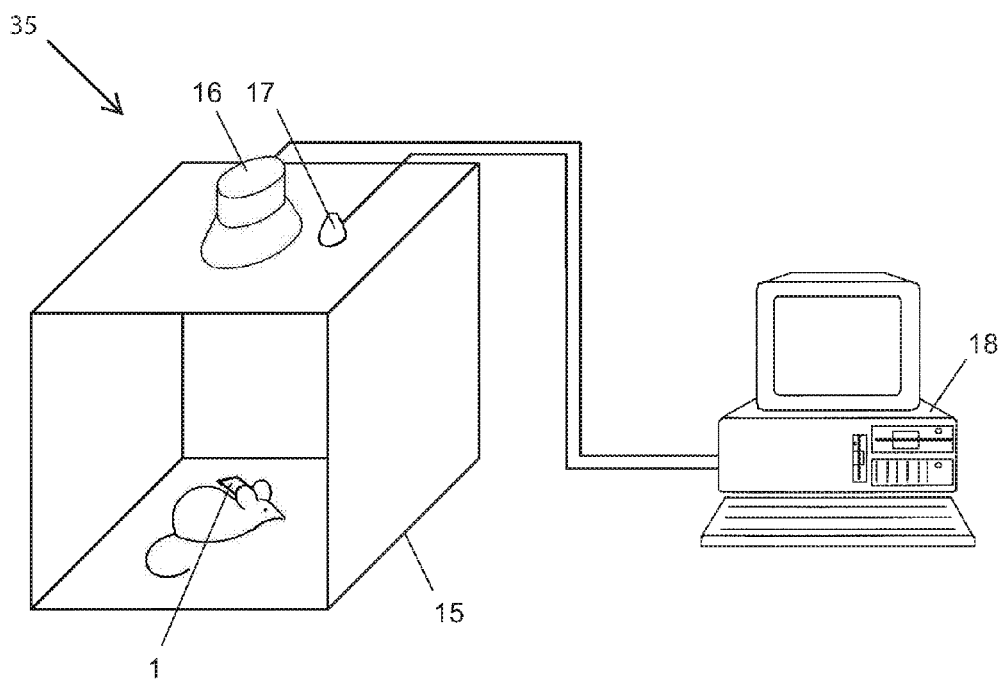
FIG. 14 represents an EEG recording system with stimulation based on proposed recorder for investigation of evoked potentials in mice.

FIG. 14 shows an experimental setup for evoked potential investigation in an animal or animals based on proposed recorder.

The setup includes an ultra-miniature recorder 1 fixed on the animal head, an experimental chamber 15 equipped with a speaker 16 and an infrared sender (emitter) 17. The speaker 16 and the infrared emitter 17 are controlled by a computer 18. The speaker 16 provides an auditory stimulation in a form of short sound sequences. Simultaneously with the presentation of auditory stimuli to the animal, the infrared emitter 17 sends a synchronizing signal to the recorder 1. The recorder 1 receives the synchronizing signal by means of the sensor 7, which in this case is an infrared receiver (in FIG. 1). Brain waves from the animal and synchronizing event labels from the sender 17 are stored in the memory module 3 of the device 1. The content of the memory is downloaded from the recorder 1 after the end of recording session for the further analysis.

This setup can be used for investigation of mismatch negativity (MMN) in mice. Mismatch negativity paradigm can reveal deviance-related electrophysiological activity. Mismatch negativity is an auditory event-related potential (ERP) that is generated when a stimulus violates the invariance or regularity of the recent auditory past. In the simplest paradigm, this is the case when an infrequent stimulus (deviant) that differs in any physical characteristic such as frequency, duration, intensity or location is presented among repeatedly presented standard stimuli. Standard and deviant tones can be used in a mirror design (deviants in one trial served as standards in the next and vice-versa). For example, accord 4+8 kHz vs. accord 3+6 kHz (frequency MMN), duration 50 ms vs. duration 150 ms (duration MMN) and mixed frequency-duration paradigm (simultaneous difference in frequency and duration, mixed MMN) can be applied. Difference waves ("deviant ERP" minus "standard ERP") are the most common form of MMN representation.

During the above-mentioned experiment, several mice equipped with ultra-miniature recorders, can be tested simultaneously. Theoretically, an unlimited number of mice can be used with one stimulating device at the same time. These mice can be placed in one cage or in separate individual cages, which depends on researcher's request. In some research, for example in mentioned above MMN study, a few mice can be placed in a single cage. MMN is supposed to be attention-independent phenomenon and the obtained results can be better (i.e., increased MMN), if animal attention will be switched from the auditory procession to social activity. Of course, if any social activity should be avoided, animals should be placed in the individual cages.

The speaker 16 can be driven by a sound card of the computer 18. The infrared sender 17 can be driven by a serial port of the computer 18 and an appropriate current amplifying circuitry. Alternatively, the synchronizing signal can be sent by a specially constructed USB-based adapter, or by a parallel (printer) port.

Often it is necessary to compare brain responses to different auditory stimuli. Such stimuli can be, for instance, just different tones, or sounds of different frequencies. However, the total amount of different sounds is limited in the experiment. Thus, the type of stimuli can be coded by a limited amount of bits. These coding bits can be sent one by one to the recorder 1 through the sender 17 after a start bit indicating the beginning of a data packet. The start bit is sent at a time point of stimulus onset. This sequence of bits is stored in the recorder 1.

The time of each stimulus presentation is known in advance in such experiment. A simple synchronization of the start of the record with the sound-generating computer could be sufficient in this situation. However, a precise timing of stimuli presentation is difficult to achieve by commonly used computer hardware, mainly because of operation system caused delays. Thus, storing synchronizing labels directly in the recorder 1 allows avoid the use of expensive professional stimulating equipment that has a precise timing.

There are some experiments in which stimuli presentation times are not known in advance and depend on animal behavior in the experiment. Thus, information about stimulating signals and animal behavior should be stored somewhere. If the external equipment has a precise timing, such information can be stored in it. However, it is much more convenient for the further analysis to store all relevant to the experiment data in one place—in the recorder 1.

Figure 15:
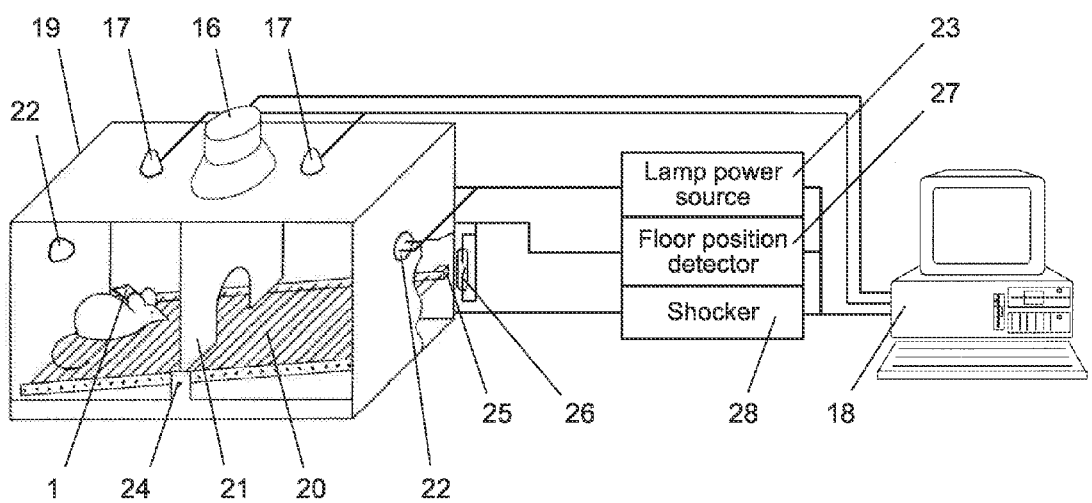
FIG. 15 shows a system based on proposed recorder for investigation of brain responses of a mouse in an operant learning paradigm—in an active avoidance task in a "Shuttle-Box".

An example of a setup in which information about stimulation and behavioral responses is transmitted to the recorder is presented in FIG. 15. A Go/NoGo sound discrimination paradigm based on 2-way avoidance equipment is taken as an example.

The system includes a metallic chamber 19 with two identical compartments, supplied with a grid floor 20. The compartments are separated by a wall 21 with an opening and are illuminated by bulbs 22 powered by a power source 23 controlled by the computer 18. The floor 20 is placed at an axis 24 with a possibility of turning around this axis, when an animal moves from one compartment to another. A small permanent magnet 25 is attached to one rear corner of the floor 20. The magnet 25 controls the ON-OFF state of a hermetically shielded switch 26, whose state is analyzed by a floor position detector 27 that sends information to the computer 18. Controllable by the computer 18, a shocker 28 can apply a small controllable current to the grid floor 20. Such current is an aversive stimulus for an animal. The chamber 19 is equipped with a speaker 16 and two of the infrared emitters 17 (one per compartment), also controllable by the computer 18. The speaker 16 is used for audio stimulation, and emitters 17 send signals to the recorder 1, as it was described earlier.

A training schedule can be the following. Go/NoGo sound frequency and sound duration discrimination paradigms are taken as examples. The animals are trained during 7 days (40 "Go" and 40 "NoGo" trails daily) to discriminate between pairs of sound (75 dB SPL, sound pressure level). In the Go/NoGo sound frequency discrimination, the "Go" signal includes two sounds: 50 ms 2.5 kHz and 50 ms 10 kHz, which are separated by 200 ms of silence. The "NoGo" signal includes two identical 50 ms 5 kHz sounds separated by 200 ms of silence. Each "Go" trial includes up to 5 "Go" signal presentations with inter-stimulus interval 1 s (onset-to-onset). However if the animal does not move to the opposite compartment, it receives additional "Go" signal presentations (maximum 5), each paired with punishment—an electric current, 200 ms, 200 μA (the onset of each 200 ms current coincides with the onset of the second sound in the sound pair). Inter-trial time interval is varying by chance in the range 5-15 s. Each "NoGo" trial includes up to 5 "NoGo" cue presentations. If the animal is moving to the opposite compartment during these 5 sec, it receives the punishment—current 200 ms, 200 μA, once. At the moment of current application, "NoGo" sound presentation is terminated even if the animal was not exposed to the whole 5 "NoGo". The order of "Go" and "NoGo" trials is pseudo-stochastic, but fixed for all animals and all training days. After 7 days of task-free period the animals can be tested in Go/NoGo sound duration discrimination task during the next 7 days. The "NoGo" signal should be taken from the previous sound frequency discrimination task. The "Go" signal includes two sounds: 50 ms 5 kHz and 150 ms 5 kHz, separated by 200 ms of silence. An animal should be able to discriminate duration of the second sounds—150 ms in "Go" and 50 ms in "NoGo". Discrimination D can be calculated as D [%]=("Correct Go"−"Mistaken Go")/40×100.

In this setup, the computer 18 has to send information of different types to the recorder 1, such as: start of audio stimulation (2 different stimuli), end of audio stimulation, start/stop of shocker (2 signals) and changes in mouse location (from the left to the right, from the right to the left). Thus, totally seven different time labels should be transmitted to the recorder 1 through senders 17. Despite having to code seven different time labels by three bits only, it is more convenient to code each label by an independent bit in a package. In such case, even if several events will occur absolutely simultaneously, information about them will be transmitted without delays introduced by a temporal overlapping of different packages. As packages are very short (8 bits), an error in timing introduced by a pair of almost simultaneous events (when a necessity to transmit the second packet arises when the first is not transmitted completely) can be neglected. Alternatively, if transmission delays are absolutely unacceptable, a transmitted package can contain a "time stamp"—a sequence of bits coding absolute time when an event occurred. In this case, even if information about an event will be transmitted with a small transmission delay, a precise time will be stored in the recorder 1.

The described example demonstrates that the proposed method of synchronization of the recorder with external equipment can also work well when a sequence of events is not known a priory and depends on animal behavior during an experiment.

Figure 16:
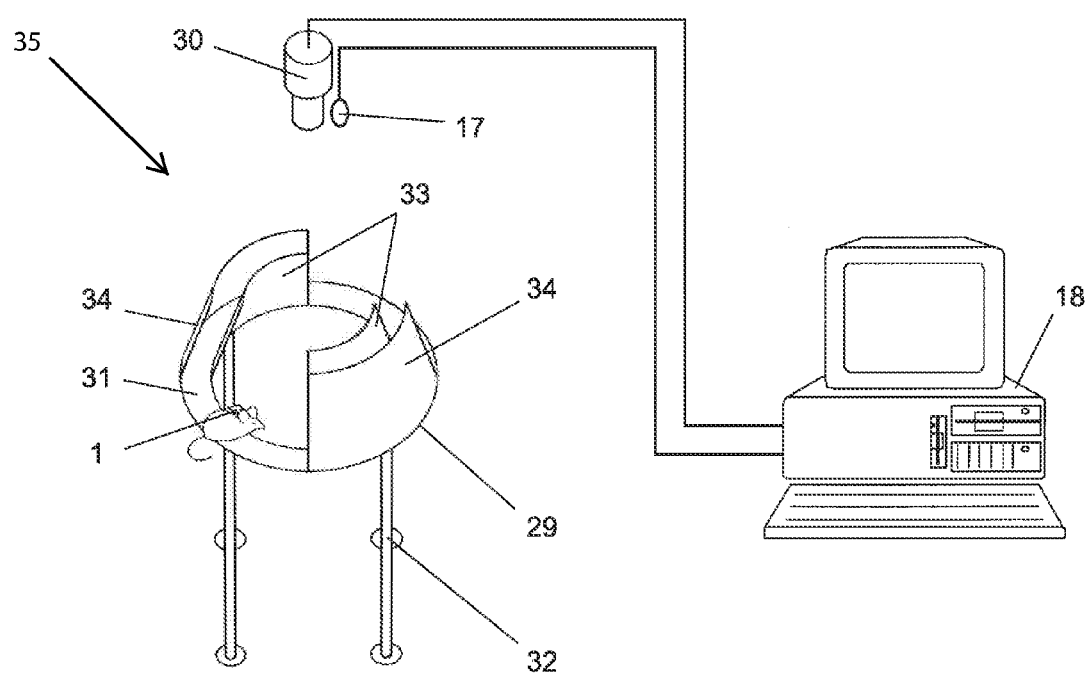
FIG. 16 shows a system based on proposed recorder for investigation of brain responses of a mouse in an anxiety/exploratory behavioral test—in an elevated O-maze.

A system based on proposed recorder for investigation of anxiety/exploratory behavior in mice is depicted in FIG. 16. It includes a recorder 1 placed at the animal's head, an infrared emitter 17 for sending signals to the recorder 1, the computer 18, an elevated O-maze 29, and a video camera 30 connected to a video grabber board placed in computer 18. A main part of the elevated O-maze 29 is a 5.5-cm-wide annual runway 31 constructed using gray plastic. It has an outer diameter of 46 cm and is placed 40 cm above the floor at four legs 32. Two opposing 90° sectors are protected by 16-cm-high inner 33 and outer 34 walls of gray polyvinyl chloride (height 16 cm). In order to make the protected sectors fully visible to the video camera, the side walls are slightly tilted towards the center.

During an experiment animals are released in one of the protected sectors and observed for 10 min. Computer 18 calculates from the received video flow coordinates of animal's gravity center and stores these XY coordinates with a frequency 4.2/s. To complement video tracking, head dipping movements are recorded using the keyboard of the computer 18 running appropriate software for event recording. When an animal changes a zone, for instance moves from an unprotected zone to a protected, the computer 18 sends to the recorder 1 through the infrared emitter 17 a short sequence of bits coding this particular event. Keystroke events are also being sent to the recorder 1 in a similar way. As a result, all necessary for analysis information was synchronized and stored in a single place—in the recorder 1. This strongly simplifies analysis of physiological/behavioral data.

The presented example nicely illustrates how the proposed recorder can be integrated in an existing behavioral setup, in which no electrophysiological recordings were done before. It is important to note that a wired connection of the subject with external equipment is impossible in such experiment as attached cable will strongly affect the investigated behavior. The philosophy of use of the recorder in this and similar setups is that animal behavior should be split into behavioral episodes and categorized or classified. At the moments when a transition of states of an animal takes place, an appropriate label should be sent to the recorder. Precise coordinates of the animal at particular moments of an experiment usually are not very easy to link with an electrical brain activity. Thus, detailed information about animal location is not very valuable for such analysis. However, if there is a need to have access to such type of information, it can be extracted from the computer 18 and synchronized with the electrophysiological data stored in the recorder by means of mentioned above labels. Alternatively, it is possible to send animal location information to the recorder, say 4.2 times per second, and store it in the recorder together with the keystroke labels.

It should be understood that the foregoing relates only to a preferred embodiment of the present invention and that numerous modifications or alterations may be made without departing from the spirit and scope of the invention as set forth in the appended claims.

What is claimed is:

1. A system for recording biological data from a small animal, comprising:
   external stationary scientific equipment having an external stationary sensor and an emitter, wherein the external stationary sensor registers animal behavior information of a small animal bearing a recorder;
   the emitter of the external stationary scientific equipment transmits the registered animal behavior information to the recorder of the same small animal bearing the recorder,
   the recorder comprising:
   a biological signal sensor configured to sense at least one biological signal from a small animal;
   a convertor configured to convert the at least one biological signal to digital data;
   a sensor configured to receive the animal behavior information sent from the emitter of the external stationary scientific equipment and to synchronize the animal behavior information with the digital data locally at the recorder;
   a data storage unit integrated to the recorder and configured to store the digital data synchronized with the animal behavior information received from the emitter of the external stationary scientific equipment locally at the recorder;
   a data output configured for transporting the stored digital data from the recorder after a recording session; and,
   a power source.

2. The system of claim 1, wherein the biological signal comprises electrical brain activity.

3. The system of claim 1, wherein the sensor configured to receive the animal behavior information from the external stationary scientific equipment is a wireless receiver.

4. The system of claim 3, wherein the sensor configured to receive the information from the external stationary scientific equipment is an acoustic sensor or an optical sensor.

5. The system of claim 4, wherein the optical sensor is an infrared sensor.

6. The system of claim 3, wherein the wireless receiver is a radio wave receiver.

7. The system of claim 1, wherein the recorder is separate from the external stationary scientific equipment.

8. The system of claim 1, wherein the recorder is wireless with respect to the external stationary scientific equipment.

9. The system of claim 1, wherein the external stationary sensor is configured to register an action of the small animal, bearing the recorder.

10. The system of claim 1, wherein the external stationary sensor is configured to register a pressing of the small animal, bearing the recorder, on a lever or a crossing of an infrared beam.

11. The system of claim 1, wherein the external stationary scientific equipment connects with a computer for processing the animal behavior information obtained from the small animal, bearing the recorder and the computer sends the animal behavior information to the recorder through the external stationary emitter.

12. The system of claim 1, wherein the stationary sensor is a video camera.

13. The system of claim 11, wherein the computer is configured to analyze the animal behavior information obtained from the small animal, bearing the recorder, split the animal behavior information into behavioral episodes, classify the behavioral episodes, and send labels of the behavioral episodes to the recorder by the external stationary emitter.

14. The system of claim 1, wherein the external stationary scientific equipment is configured to acquire the animal behavior information from the small animal, bearing the recorder, wherein the external stationary scientific equipment configured to send the animal behavior information obtained from the small animal, bearing the recorder, to the recorder, and the data storage unit configured to store the animal behavior information obtained from the external stationary scientific equipment and acquired by the external stationary scientific equipment from the small animal, bearing the recorder.

15. The system according to claim 1, wherein the external stationary scientific equipment is configured to store the animal behavior information obtained from the small animal, bearing the recorder, prior to sending it to the recorder.

16. The system according to claim 1, wherein a computer receives the animal behavior information from a video camera, and the emitter sends the animal behavior information to the recorder.

17. The system according to claim 1, wherein the external stationary sensor is a video camera that records the animal behavior information, and the video camera connects with a computer.

18. A method of measuring physiological variables in a small animal, comprising:
   providing external stationary scientific equipment having an external stationary sensor and an emitter, wherein the external stationary sensor registers animal behavior information of a small animal bearing a recorder, and the emitter of the external stationary scientific equipment transmits the registered animal behavior information to the recorder of the same small animal bearing the recorder, providing the recorder comprising: a biological signal sensor configured to sense at least one biological signal from the small animal; a converter configured to convert the at least one biological signal to digital data; a sensor configured to receive information sent from external stationary scientific equipment and to synchronize the information with the digital data locally at the recorder; a data storage unit integrated to the recorder and configured to store the digital data synchronized with the information received from the external stationary scientific equipment locally at the recorder; a data output configured for transporting stored data from the recorder after a recording session, and a power source;

fixing the recorder to the small animal;

registering the animal behavior information by the external stationary sensor of the external stationary scientific equipment;

sending the animal behavior information from the emitter of the external stationary scientific equipment to the recorder;

acquiring the at least one biological signal from the small animal via the biological signal sensor;

converting the at least one biological signal to the digital data;

receiving the animal behavior information from the external stationary scientific equipment locally at the recorder; and, synchronizing the animal behavior information with the digital data locally at the recorder.

19. The method of claim 18, wherein the animal behavior information from the external stationary scientific equipment is transmitted to the recorder wirelessly.

20. The method of claim 18, wherein the animal behavior information from the external stationary scientific equipment is set by an action of the small animal, bearing the recorder.

21. The method of claim 20, wherein the action of the small animal, bearing the recorder, is a pressing on a lever or is a crossing of an infrared beam.

22. The method of claim 18, wherein a computer receives the animal behavior information, analyzes the animal behavior information, splits the animal behavior information into behavioral episodes, classifies the behavioral episodes, and sends labels of the behavioral episodes to the recorder via the emitter.

23. The method according to claim 18, further comprising storing the animal behavior information obtained from the small animal, bearing the recorder, at the external stationary scientific equipment prior to sending it to the recorder.

24. A system for recording biological data from a small animal, comprising:

external stationary scientific equipment having a user interface and an emitter, wherein animal behavior information is obtained from a small animal bearing a recorder and inputted by an operator or an observer into the user interface of the external stationary scientific equipment, and the emitter of the external stationary scientific equipment transmits the inputted animal behavior information to the recorder of the same small animal bearing the recorder, the recorder comprising:

a biological signal sensor configured to sense at least one biological signal from a small animal;

a convertor configured to convert the at least one biological signal to digital data;

a sensor configured to receive the animal behavior information inputted into the user interface and sent from the emitter of the external stationary scientific equipment and to synchronize the animal behavior information with the digital data locally at the recorder;

a data storage unit integrated to the recorder and configured to store the digital data synchronized with the animal behavior information received from the emitter of the external stationary scientific equipment locally at the recorder;

a data output configured for transporting the stored digital data from the recorder after a recording session; and, a power source.

25. The system of claim 24, wherein the operator or observer analyzes the animal behavior information obtained from the small animal, bearing the recorder, splits the animal behavior information into behavioral episodes, classifies the behavioral episodes, and sends labels of the behavioral episodes to the recorder by the external stationary emitter, wherein the labels are stored in the recorder.

26. A system for recording biological data from a small animal, comprising:

external stationary scientific equipment having an external stationary stimulator to provide stimulation to a small animal bearing a recorder and an emitter, and the emitter of the external stationary scientific equipment transmits animal stimulation information to the recorder of the same small animal bearing the recorder, the recorder comprising:

a biological signal sensor configured to sense at least one biological signal from a small animal;

a convertor configured to convert the at least one biological signal to digital data;

a sensor configured to receive the animal stimulation information sent from the emitter of the external stationary scientific equipment and to synchronize the animal stimulation information with the digital data locally at the recorder;

a data storage unit integrated to the recorder and configured to store the digital data synchronized with the animal stimulation information received from the emitter of the external stationary scientific equipment locally at the recorder;

a data output configured for transporting the stored digital data from the recorder after a recording session; and, a power source.

27. The system of claim 26, wherein the emitter is configured to send the animal stimulation information to the recorder simultaneously with the stimulation provided to the small animal, bearing the recorder, by the external stationary stimulator.

28. The system of claim 26, wherein the external stationary stimulator is configured to provide a light stimulation, a sound stimulation, or an electric stimulation.

29. The system of claim 28, wherein a grid floor supplies the electric stimulation to the small animal, bearing the recorder.

30. The system for recording biological data from a small animal according to claim 26, wherein the external stationary scientific equipment is configured to store the animal stimulation information prior to sending it to the recorder.

* * * * *